(12) United States Patent
LeFevere et al.

(10) Patent No.: US 10,416,061 B2
(45) Date of Patent: Sep. 17, 2019

(54) BLANK WASHER INSPECTION SYSTEM

(71) Applicants: Michael W LeFevere, Imlay City, MI (US); Raymond Slowik, Royal Oak, MI (US)

(72) Inventors: Michael W LeFevere, Imlay City, MI (US); Raymond Slowik, Royal Oak, MI (US)

(73) Assignee: FCA US LLC

( * ) Notice: Subject to any disclaimer, the term of this patent is extended or adjusted under 35 U.S.C. 154(b) by 0 days.

(21) Appl. No.: 15/836,297

(22) Filed: Dec. 8, 2017

(65) Prior Publication Data

US 2019/0178776 A1 Jun. 13, 2019

(51) Int. Cl.
G01N 15/06 (2006.01)
G01N 21/88 (2006.01)

(52) U.S. Cl.
CPC ..... *G01N 15/0625* (2013.01); *G01N 21/8803* (2013.01); *G01N 21/8851* (2013.01); *G01N 2201/10* (2013.01)

(58) Field of Classification Search
CPC .......... G01N 15/0625; G01N 21/8803; G01N 21/8851; G01N 2201/10; G01N 21/8806; G01N 21/9501; G01N 2021/845; G01N 2021/8867; G01N 21/6428; G01N 21/6456; G01N 33/442; G01N 2001/028; C04B 41/52; G03F 7/2004; G03F 1/24; G03F 1/60; G03F 1/48
See application file for complete search history.

(56) References Cited

U.S. PATENT DOCUMENTS

| | | | | |
|---|---|---|---|---|
| 5,128,719 A * | 7/1992 | Umeda | .............. | G03G 15/0266 399/161 |
| 6,025,206 A * | 2/2000 | Chen | .................. | G01N 21/9501 250/559.41 |
| 6,630,996 B2 * | 10/2003 | Rao | ..................... | G01N 21/9501 356/237.1 |
| 7,172,804 B2 * | 2/2007 | Kelso | ................... | B01J 19/0046 428/195.1 |
| 7,262,425 B2 * | 8/2007 | Nishiyama | ........... | G01N 21/274 250/559.4 |
| 8,189,205 B2 * | 5/2012 | Miyoshi | ............... | G01B 11/303 356/600 |
| 9,638,643 B2 * | 5/2017 | De Jong | ............... | G03F 7/7085 |

(Continued)

FOREIGN PATENT DOCUMENTS

KR 20160006378 * 1/2016 ............. B23K 26/21

*Primary Examiner* — Mohammed K Amara
(74) *Attorney, Agent, or Firm* — Ralph E. Smith

(57) ABSTRACT

In at least one implementation, a blank washer inspection process includes the steps of: applying at least one test particle to a blank; washing the blank having the test particle thereon; inspecting the blank after it has been washed to identify any test particle on the blank; and comparing any test particle identified in the inspection step to a threshold. The threshold may relate to a control property of the test particle. In at least some implementations, the control property is the size of the particle and a maximum size may be set as a threshold. Other control properties may be used. Further the test particles may include detection properties to facilitate identifying test particles and distinguishing among test particles in different groups.

16 Claims, 3 Drawing Sheets

(56) References Cited

U.S. PATENT DOCUMENTS

| | | | |
|---|---|---|---|
| 2002/0198928 A1* | 12/2002 | Bukshpan | B01L 3/502761 709/200 |
| 2003/0041678 A1* | 3/2003 | Hoshida | G01N 33/442 73/866 |
| 2005/0018899 A1* | 1/2005 | Elyasaf | G01N 21/8851 382/145 |
| 2005/0116397 A1* | 6/2005 | Kimura | B24C 3/14 266/135 |
| 2006/0091334 A1* | 5/2006 | Urbach | G01N 21/9501 250/559.45 |
| 2006/0138368 A1* | 6/2006 | Lee | G01N 21/9501 250/559.45 |
| 2006/0181700 A1* | 8/2006 | Andrews | G01N 21/21 356/237.2 |
| 2006/0204997 A1* | 9/2006 | Macioszek | C12Q 1/6851 435/6.11 |
| 2006/0257992 A1* | 11/2006 | McDevitt | B01L 3/502715 435/287.2 |
| 2007/0291257 A1* | 12/2007 | Benjamin Tsai | G01N 21/8806 356/73 |
| 2008/0213133 A1* | 9/2008 | Wallace | B01L 3/5023 422/82.05 |
| 2008/0250877 A1* | 10/2008 | Wu | G01N 1/14 73/864.33 |
| 2009/0073440 A1* | 3/2009 | Tiemeyer | G01N 21/9501 356/338 |
| 2009/0184257 A1* | 7/2009 | Shakespeare | G01J 3/36 250/459.1 |
| 2009/0289183 A1* | 11/2009 | Chen | G01N 1/02 250/282 |
| 2009/0290920 A1* | 11/2009 | Hatakeyama | G03G 21/0094 399/346 |
| 2009/0302235 A1* | 12/2009 | Himmelhaus | G01N 21/6428 250/458.1 |
| 2009/0320619 A1* | 12/2009 | Bunker | G01N 1/2202 73/863.22 |
| 2011/0027558 A1* | 2/2011 | Kirby | C04B 41/009 428/215 |
| 2011/0237162 A1* | 9/2011 | Kostevich | B24C 7/0038 451/38 |
| 2012/0182538 A1* | 7/2012 | Koole | G01N 21/6428 355/75 |
| 2013/0027540 A1* | 1/2013 | Ito | G01B 11/08 348/79 |
| 2015/0111199 A1* | 4/2015 | Hart | G01N 21/47 435/5 |
| 2015/0226539 A1* | 8/2015 | Roeth | G01B 11/005 356/614 |
| 2016/0004153 A1* | 1/2016 | Shoki | G03F 1/24 204/192.13 |
| 2016/0245792 A1* | 8/2016 | Funk | G01N 33/84 |
| 2018/0017480 A1* | 1/2018 | Fukuda | G01N 15/14 |
| 2018/0040474 A1* | 2/2018 | Zi | B08B 3/08 |
| 2018/0045628 A1* | 2/2018 | Etchin | G01N 1/38 |
| 2018/0195960 A1* | 7/2018 | Goix | G01N 21/6428 |
| 2019/0120727 A1* | 4/2019 | Harding | G01N 33/00 |

* cited by examiner

BLANK WASHER INSPECTION SYSTEM

FIELD

The present disclosure relates to a system for washing and inspection of blanks of material.

BACKGROUND

Metal blanks, such as sheet metal, often arrive at a manufacturing facility with a coating of mill oil on them which protects the blanks from corrosion and inhibits rust. Various contaminants like dust, dirt, and other particles may find their way onto the blanks and may become stuck in the mill oil or otherwise stuck on the blanks. Prior to forming the blanks into a desired product, the blanks are often cleaned to remove the contaminants and often the mill oil. This often includes passing the blanks through a wash station that may include brushes, rollers, wipers and the like, as well as water and cleaning solvents or detergents, if desired. Visual inspection of the washed blanks can be difficult and contaminants that remain on the blanks may result in larger imperfections when the blank is drawn, stamped or otherwise formed. These imperfections can render the part unusable or require time consuming, manual and often expensive repairs to the part.

Further, the existence of a defect does not necessarily mean the wash station did not perform properly because contaminants can find their way onto the blanks after the blanks are washed. Thus, it is difficult to determine if the wash station is operating correctly and if not, what the problem is. This often leads to more parts being formed with defects before the existence of a problem is identified and then the problem is determined.

SUMMARY

In at least one implementation, a blank washer inspection process includes the steps of:
  applying at least one test particle to a blank;
  washing the blank having the test particle thereon;
  inspecting the blank after it has been washed to identify any test particle on the blank; and
  comparing any test particle identified in the inspection step to a threshold. The threshold may relate to a control property of the test particle. In at least some implementations, the control property is the size of the particle and a maximum size may be set as a threshold. Presence after a blank has been washed of a particle of a size greater than the threshold indicates that the blank was not satisfactorily washed. Other control properties may be used. Further the test particles may include detection properties to facilitate identifying test particles and distinguishing among test particles in different groups.

In at least some implementations, a blank washer inspection system, includes a supply of test particles, an application station and an inspection area. The test particles may have at least one control property and at least one detection property. Multiple test particles are applied to a blank at the application station prior to washing the blank. The blanks are inspected in the inspection area after the blanks are washed to detect the presence of test particles remaining on the blank after the blank was washed.

Further areas of applicability of the present disclosure will become apparent from the detailed description, claims and drawings provided hereinafter. It should be understood that the summary and detailed description, including the disclosed embodiments and drawings, are merely exemplary in nature intended for purposes of illustration only and are not intended to limit the scope of the invention, its application or use. Thus, variations that do not depart from the gist of the disclosure are intended to be within the scope of the invention.

DETAILED DESCRIPTION

Figure 1:
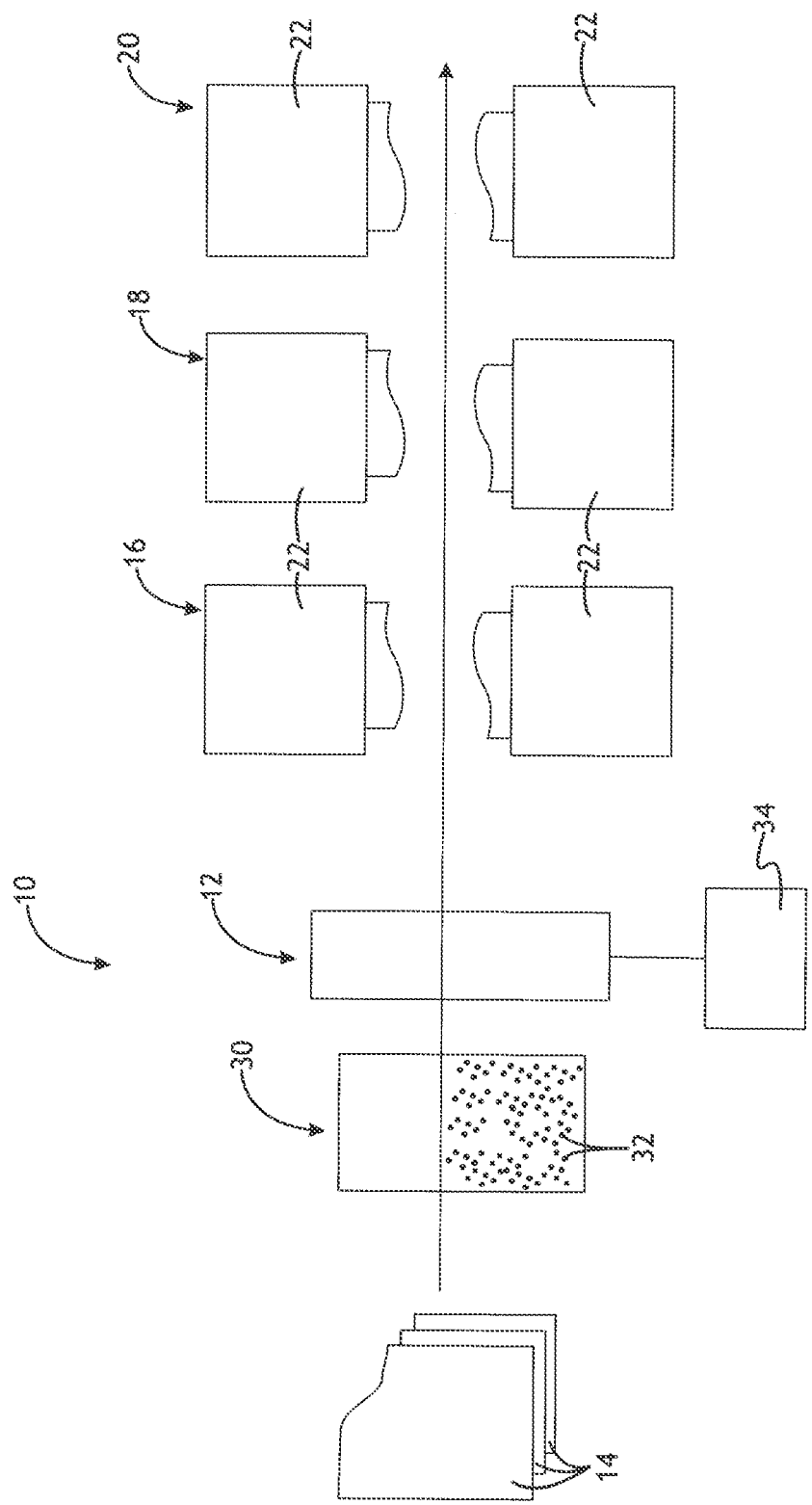
FIG. 1 is a schematic view of a blank washer and inspection system, and downstream workstations.

Referring in more detail to the drawings, FIG. 1 diagrammatically illustrates a blank washer and inspection system 10 for determining and improving the operation of a blank washer or wash station 12. Metal blanks 14, such as sheet metal, are arranged to be cleaned at a wash station 12 and prepared for various forming processes such as drawing, trimming, flange formation and others, as diagrammatically illustrated by workstations 16, 18 and 20 in FIG. 1, arranged in series and including various forming dies 22.

During the washing step, the blanks 14 are washed to remove mill oil and contaminants such as dust, dirt and other contaminants. This often includes passing the blanks 14 through the wash station 12 that may include brushes, rollers, wipers and the like, as well as water and cleaning solvents or detergents, if desired. While a perfectly clean blank 14 that is free of any contaminant of any size if not often the goal, a blank 14 that is clean enough for subsequent processing and forming operations without creating a noticeable or unacceptable part deviation is often the goal. After the blanks 14 have been washed, they may be lubricated with any desired lubrication, if desired.

Figure 2:
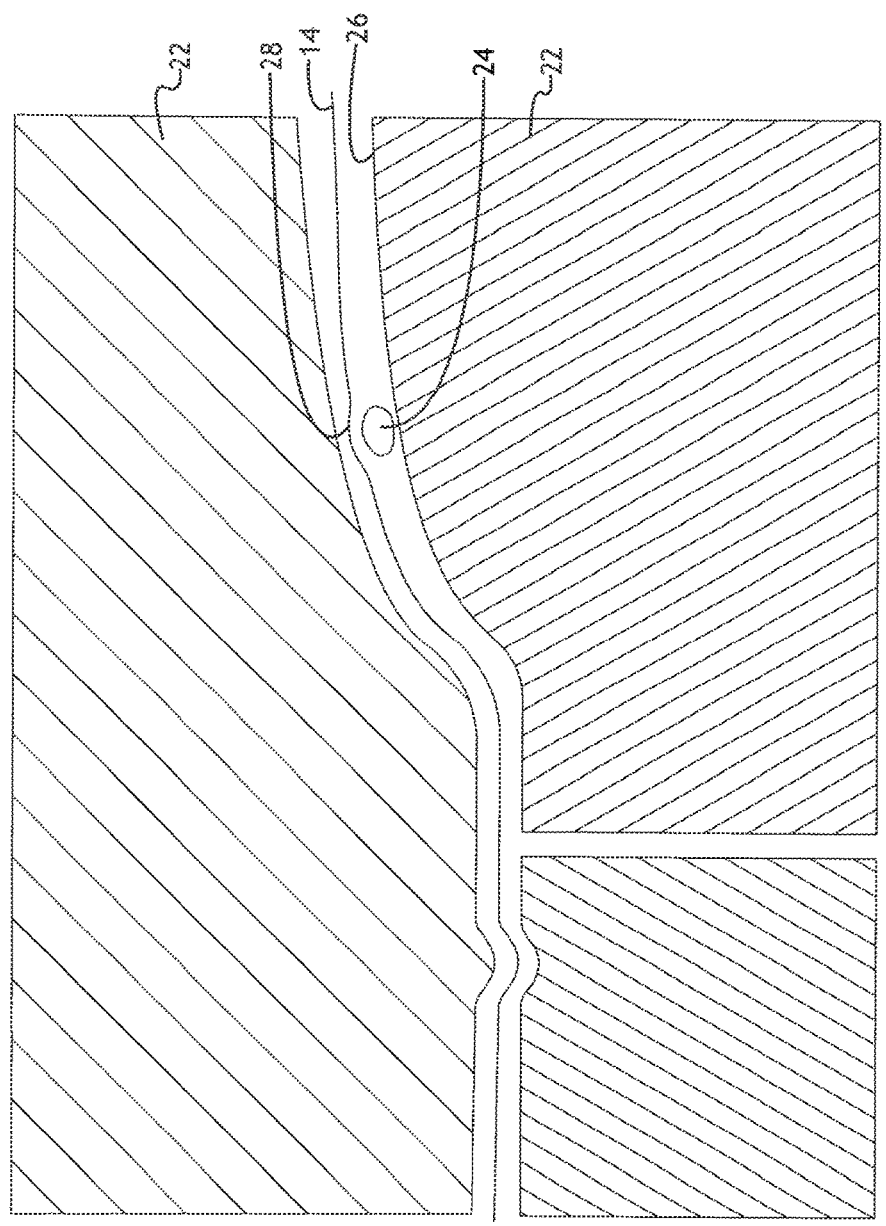
FIG. 2 is an enlarged, fragmentary diagrammatic view of a blank in between dies of a forming die and a contaminant between the blank and a forming die.

Hence, the washing station 12 may be designed to achieve a particular result, which may relate to removal from the blanks of all, or substantially all, particles above a certain threshold size as larger particles are likely to cause larger defects in subsequent processing. For example, during a stamping or drawing operation as shown in FIG. 2, the blank 14 may be received between two dies 22 so that the blank is formed between opposed die forming surfaces. If a particle 24 is on the blank 14, it will be trapped between a die forming surface 26 and the blank 14 and can create a high spot, discontinuity in the blank surface or other imperfection 28 in the blank, as shown in FIG. 2. Imperfections of a certain magnitude may be unacceptable in certain parts and acceptable in other parts, so the blank washing station 12 may have different end requirements for different blanks.

In at least some implementations, the blank washer and inspection system 10 includes a test particle supply 30 located upstream of the wash station 12. The test particle supply 30 includes a supply of test particles 32 that are applied to at least part of one or more surfaces of a blank 14 before the blank is washed. The test particles 32 may be applied in any suitable manner, including but not limited to, roller, brush, spreader, or spray applicators. The test particles may be applied evenly over a desired portion or all of the blank 14, or the test particles may be applied unevenly, as desired. Uneven and even test particle application may both be used on different portions of the blank, and different application methods may be used on the same blank as well to provide test particles in different arrangements and concentrations on the blank, as desired.

In at least some implementations, the test particles 32 have at least one detection property that facilitates identification of the presence of the test particle after the blank 14 has been washed so that inadequate removal of the test particles can more easily be determined compared to uncontrolled contaminants (e.g. particles and things on the blank not applied at the test particle application station). For example, the detection property that facilitates identification of the test particle 32 may be a visual property, such as a color, light reflectivity or luminescence under at least certain wavelengths of light. Other detection properties may be magnetic and detected by a magnetic pickup device that could be examined for accumulation. Additionally or instead, the test particles may be chemically treated to react with a second chemical agent, and detection could be done via a chemically treated swab or wipe which would change visually, chemically or in some other way due to a reaction from or with the test particles. Similarly, chemically treated test particle residue could be detected via an application of a chemically activating developing agent which again changes color or luminance or some other property upon activation.

Further, the test particles 32 may be uniform, that is, of the same size, shape, density, hardness and the like, or the test particles may have varying properties and characteristics as desired. In at least some implementations, test particles 32 with varying control properties and characteristics are used together and applied to a blank at the same time (e.g. one after another, or as a mixture) to determine the performance of the wash station against different contaminants.

To facilitate detection of the test particles 32, they may be provided or arranged in groups with each group having at least one control property to facilitate determination of the group or type of test particle on the blank 14. For example, test particles in a first group may be larger than 50 microns in size and may be of a first color (i.e. the control property relates to size). Test particles in a second group may be at least 40 micron but less than 50 microns in size, and these test particles may be of a second color that is different than the first color. Other groups with other sizes of test particles may also be provided, for example, a third group of a still different size and of a third color that is different than both the first color and the second color. In this example, the sizes may be a maximum dimension of the test particle taken along a maximum cross-sectional area of the test particle. Of course, other measurement techniques or parameters may be used as desired. The test particles may be spherical or irregularly shaped, may be solid, have cavities, or be otherwise formed as desired.

In addition to or instead of size, the test particles 32 may have other control properties used to check the performance of the wash station 12. For example, the hardness of the test particles 32 may be within a desired range, or within different ranges where more than one group is used. Here again, each group may have a different detection property to facilitate detection of test particles within each group. Other control properties that may be varied among groups of test particles or controlled within a single group includes, but are not limited to, hardness, surface texture or surface finish, dimensionality or shape, and liquid absorption (e.g. wash solution, oil, etc—some particles might absorb some, none or at different rates than other particles). Control properties may be made from specific materials or fluids native to a particular machine system, as identified in a library of native material and liquids. Detection method can be tailored to detect those specific native materials or liquids. It may be desirable if the test particles 32 do not dissolve in the liquids used to wash the blank, if the test particles do not foul the liquids and if the test particles can be readily filtered out or otherwise separated from the liquids so that further use of the wash station does not introduce the test particles onto subsequent blanks in the wash station, or so that the test particles may be used again.

After the desired test particles 32 have been applied to all or a portion of the blank 14 to be washed, the blank is washed at the wash station 12 and then the blank is inspected after washing in an inspection area 34 and before the blank is moved through any post-wash forming stations (e.g. 16, 18, 20). Inspection of the blank 14 may be accomplished in various ways by one or more people or machines and the area can be a clean room to prevent or limit other contaminants from affecting the inspection, or any desired area. The inspection may include, but is not limited to, visual inspection, surface scanning with a camera or other detector or sensor, and physical inspection such as by wiping the surface of the blank.

The blank inspection may be facilitated by the detection property associated with the test particles applied to the blank 14. In the example where the test particles are of a particular color or colors, reflectivity or luminescence, the test particles may be relatively easy to see upon visual inspection either by a machine or a person. Further, wiping the surface of the blank 14 will transfer at least some of any test particles 32 that remain on the blank after washing from the blank to the material used to wipe the blank. The wiping material may be chosen to readily collect the test particles, and to provide a contrasting background so that the test particles can be easily seen on the wiping material. For example, the test particles may all be of a color other than white and a white piece of material may be used to wipe the blank. Any test particles transferred to the wiping material would be relatively easy to see on the wiping material due to the color difference between the test particle and wiping material. The wiping may occur over the entire blank, or just a portion of the blank which may then be deemed to represent the condition of the entire blank.

Upon detection of test particles on the blank 14 after the blank has been washed, a decision may be made as to whether the blank was satisfactorily washed. The decision may be made based on various criteria related to the type and or quantity of test particle identified on the blank 14. In at least some implementations, presence of any test particle outside of a threshold, for example, larger than a threshold size, may warrant a decision that the blank was not satisfactorily washed. In some implementations, the test particles applied to the blank 14 may all be outside of the threshold such that identification of any test particle indicates that the blank was not satisfactorily washed. Or the test particles may be provided in various sizes and only one or more of the sizes is outside of the threshold so that detection or identification of only certain of the test particles indicates that the blank 14 was not satisfactorily washed and identification of other of the test particles might not indicate that the blank was not satisfactorily washed. In other implementations, the threshold may relate to the number of test particles that remain where no single test particle is a problem by itself, but multiple test particles on the blank, or the inspected area of the blank, is a problem. For example, the threshold in one implementation might be a size of 40 microns and any test particle over 40 microns that is detected on the blank 14 after washing indicates that the blank was not satisfactorily washed. However, a separate threshold may apply to contaminants less than 40 microns in size but larger than 30 microns. Again, by way of example, detection of 10 or more test particles in this size range on the blank 14 or a portion of the blank indicates that the blank was not satisfactorily washed, but detection of fewer than 10 such test particles is satisfactory.

Figure 3:
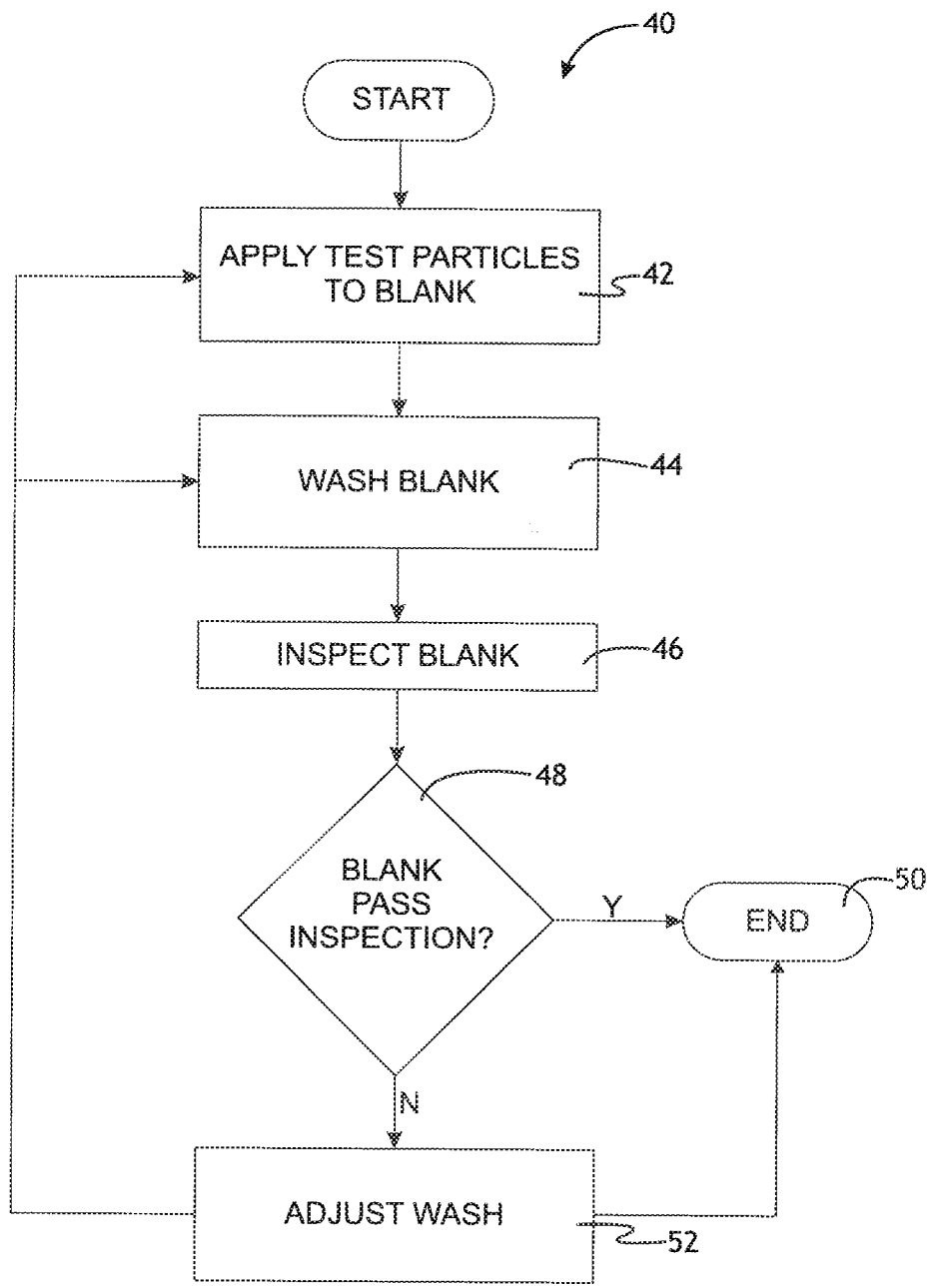
FIG. 3 is a flow chart of a blank washer inspection process.

FIG. 3 illustrates one process 40 that may be used to determine if a wash station is satisfactorily washing blanks. First, one or more test particles are applied to a blank at 42 and then the blank is washed at 44. After the blank is washed, the blank is inspected at 46 and the inspection results are compared at 48 to a threshold to determine if the blank was satisfactorily washed. If the inspection result is that the blank was deemed to be satisfactorily washed, then the process ends at 50. Liquids used in the wash station may be filtered or otherwise processed to remove the test particles and permit the liquids to be used again without test particles therein. The test particles recovered from the wash liquids can be discarded or used again, as desired. If the inspection result is that the blank was deemed to not have been satisfactorily washed, then the wash station may be adjusted or serviced to improve the performance. In particular, a pattern of poor performance (e.g. multiple blanks not satisfactorily washed) may suggest repair or replacement of brushes, water nozzles or other equipment in the wash station to improve wash performance.

The process and system may use one or more test particles to test the wash station performance. When multiple test particles are used they may all have similar control and detection properties, or they may differ. For example, a first test particle may have a first control property (e.g. a first size) and a first detection property (e.g. a first color) and a second test particle may have a second control property that is different than the first control property (e.g. a different size), and the second test particle also has a second detection property that is different than the first detection property (e.g. a different color). This facilitates not only detection of test particles, but distinguishing among groups or types of test particles to aid in blank inspection and determination of the blank wash station performance.

What is claimed is:

1. A blank washer inspection process, comprising:
   applying at least one test particle to a blank where the at least one test particle is not used to deform or in the process of performing work on the blank and the at least one test particle has a control property or a detection property, and the control property or detection property are selected prior to application of the test particles to the blank;
   washing the blank having the at least one test particle thereon;
   inspecting the blank after it has been washed to identify any of the at least one test particle on the blank; and
   comparing any of the at least one test particle identified in the inspection step to a threshold and adjusting a parameter of the washing step if at least one test particle identified in the inspection step is beyond a threshold.

2. The process of claim 1 wherein the step of applying the at least one test particle includes applying multiple test particles to the blank.

3. The process of claim 2 wherein the multiple test particles all have a detection property that is the same.

4. The process of claim 3 wherein the detection property is outside of the threshold used in the comparing step.

5. The process of claim 3 wherein the threshold relates to a maximum size of the test particles.

6. The process of claim 2 wherein the multiple test particles have different control properties.

7. The process of claim 6 wherein the test particles vary as to at least one of size, surface finish, density, shape, hardness, or liquid absorption.

8. A blank washer inspection process, comprising:
   applying at least one first test particle and at least one second test particle to a blank;
   washing the blank having the at least one first test particle and the at least one second test particle thereon;
   inspecting the blank after it has been washed to identify any of the at least one test particle on the blank; and
   comparing any of the at least one test particle identified in the inspection step to a threshold, wherein the at least one first test particle has a first control property and a first detection property that are selected prior at application of the at least one first test particle to the blank, and the at least one second test particle has a second control property that is different than the first control property, and the second test particle also has a second detection property that is different than the first detection property.

9. The process of claim 8 wherein the first detection property and second detection property are at least one of color, magnetism, chemical change, or luminescence.

10. The process of claim 1 wherein said adjusting step is performed as a function of the particular threshold that is exceeded by the at least one test particle identified in the inspection step to improve the washing step as to particles that exceed the particular threshold.

11. A blank washer inspection system, comprising:
    a supply of test particles having at least one control property and at least one detection property,
    an application station at which multiple test particles are applied to a blank prior to washing the blank where the test particles do not deform or change the material properties of the blank; and
    an inspection area wherein the blanks are inspected after the blanks are washed to detect the presence of test particles remaining on the blank after the blank was washed.

12. The system of claim 11 wherein the supply of test particles includes multiple first test particles each having a first control property and a first detection property, and multiple second test particles that each have a second control property that is different than the first control property, and each second test particle also has a second detection property that is different than the first detection property.

13. The system of claim 12 wherein the first control property is a maximum size of the first test particles and the second control property is a maximum size of the second test particles that is greater than the maximum size of the first test particles.

14. The system of claim 11 wherein said at least one detection property is visually detectable.

15. The system of claim 14 wherein the detection property is at least one of magnetism, chemical change, color, or luminescence.

16. The system of claim 11 wherein said at least one control property is at least one of size, surface finish, density, shape, hardness, or liquid absorption.

\* \* \* \* \*